United States Patent
Senaratne et al.

(10) Patent No.: US 12,195,781 B2
(45) Date of Patent: *Jan. 14, 2025

(54) MANAGEMENT OF ETHANOL CONCENTRATION DURING SYNGAS FERMENTATION

(71) Applicant: JUPENG BIO (HK) LIMITED, Sheung Wan (CN)

(72) Inventors: Ryan Senaratne, Fayetteville, AR (US); Song Liu, Fayetteville, AR (US)

(*) Notice: Subject to any disclaimer, the term of this patent is extended or adjusted under 35 U.S.C. 154(b) by 0 days.

This patent is subject to a terminal disclaimer.

(21) Appl. No.: 13/660,518

(22) Filed: Oct. 25, 2012

(65) Prior Publication Data

US 2013/0149693 A1 Jun. 13, 2013

Related U.S. Application Data

(60) Provisional application No. 61/569,355, filed on Dec. 12, 2011.

(51) Int. Cl.
| | | |
|---|---|---|
| C12P 7/14 | (2006.01) | |
| C12P 7/06 | (2006.01) | |
| C12P 7/08 | (2006.01) | |

(52) U.S. Cl.
CPC ............. *C12P 7/14* (2013.01); *C12P 7/065* (2013.01); *C12P 7/08* (2013.01); *Y02E 50/10* (2013.01)

(58) Field of Classification Search
CPC ......... Y02E 50/17; Y02E 50/10; Y02E 50/16; Y02E 50/13; C12P 7/06; C12P 7/065; C12P 7/10; C12P 7/08; C12P 7/14; C12M 21/12; C12M 23/58; C12M 29/00; C12M 29/18; C12M 43/02; C12M 47/10; C12F 3/04;

(Continued)

(56) References Cited

U.S. PATENT DOCUMENTS

| | | | |
|---|---|---|---|
| 4,511,437 A | * | 4/1985 | Heck et al. |
| 7,285,402 B2 | | 10/2007 | Gaddy et al. |
| 2003/0211585 A1 | * | 11/2003 | Gaddy et al. |

(Continued)

FOREIGN PATENT DOCUMENTS

| | | | | |
|---|---|---|---|---|
| CA | 2692733 A1 | * | 1/2009 | ............ C01B 3/382 |
| WO | WO 98/00558 | * | 1/1998 | ............... C12P 1/00 |
| WO | WO 2009/064200 | * | 5/2009 | |

OTHER PUBLICATIONS

Kundiyana et al. Syngas fermentation in a 100-L pilot scale fermentor: Design and process considerations. Journal of Bioscience and Bioengineering, vol. 109 No. 5, 492-498, 2010. (Year: 2010).*

(Continued)

*Primary Examiner* — Sean C. Barron
(74) *Attorney, Agent, or Firm* — Menqui Zheng; James P. Krueger

(57) ABSTRACT

A process is provided for management of ethanol concentration during syngas fermentation. A process for fermentation of syngas includes inoculating a medium to provide an inoculated medium. Inoculated medium is contacted with syngas and cells and medium are removed and separated to provide concentrated cells and permeate. Ethanol is separated from the permeate to provide ethanol and a reduced ethanol aqueous stream. The reduced ethanol aqueous stream is returned to the fermentation.

3 Claims, 8 Drawing Sheets

(58) Field of Classification Search
CPC ........... C12U 3/00; C07C 31/08; C12R 1/145; C12R 1/01
See application file for complete search history.

(56) References Cited

U.S. PATENT DOCUMENTS

| | | |
|---|---|---|
| 2008/0032373 A1* | 2/2008 | Bhargava et al. |
| 2008/0176301 A1* | 7/2008 | Granda et al. |
| 2009/0191593 A1* | 7/2009 | Burk et al. |
| 2010/0159551 A1* | 6/2010 | Redford |

OTHER PUBLICATIONS

Youseni et al. Liquid fuel production from synthesis gas via fermentation process in a continuous tank bioreactor (CSTBR) using Clostridium Ijungdahlii. Iranian Journal of Biotechnology, vol. 4, No. 1, Jan. 2006. (Year: 2006).*
University of Arkansas DOE article. Biologigal Production of Ethanol From Goal. DOE/PC/89876-T5, 31 pages, Aug. 14, 1992. (Year: 1992).*
Maedeh Mohammadi et al: "Bioconversion of synthesis gas to second generation biofuels: A review," Renewable and Sustainable Energy Reviews, Elseviers Science, New York, NY, US, vol. 15, No. 9, Jul. 5, 2011 (Jul. 5, 2011), pp. 4255-4273.
International Searching Authority, Partial International Search Report issued in PCT/US2012/068418, mailed Oct. 8, 2013, 1 page.

* cited by examiner

MANAGEMENT OF ETHANOL CONCENTRATION DURING SYNGAS FERMENTATION

This application claims the benefit of U.S. Provisional Application No. 61/569,355, which was filed on Dec. 12, 2011, and which is incorporated in its entirety herein by reference.

A process is provided for management of ethanol concentration during syngas fermentation. More specifically, cells and medium are removed from a fermentor and a reduced ethanol aqueous stream is returned to the fermentor at a rate effective to maintain a desired ethanol concentration.

BACKGROUND

Anaerobic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

The CO is often provided to the fermentation as part of a gaseous substrate in the form of a syngas. Gasification of carbonaceous materials to produce producer gas or synthesis gas or syngas that includes carbon monoxide and hydrogen is well known in the art. Typically, such a gasification process involves a partial oxidation or starved-air oxidation of carbonaceous material in which a sub-stoichiometric amount of oxygen is supplied to the gasification process to promote production of carbon monoxide as described in WO 2009/154788.

Ethanol concentration increases during fermentation. Certain levels of ethanol become inhibitory and result in reactor failure or decreased productivity. Processes are needed which are effective for balancing ethanol removal with maintaining desired cell density levels and ethanol productivity.

SUMMARY

A process for fermentation of syngas includes inoculating a medium to provide an inoculated medium having cell density of at least about 0.1 grams per liter. Cells and medium are removed and separated to provide concentrated cells and permeate. Ethanol is separated from the permeate to provide ethanol and a reduced ethanol aqueous stream. The reduced ethanol aqueous stream is returned to the fermentation. In an important aspect, a ratio of a rate of providing the reduced ethanol aqueous stream to the fermentation to a rate of removing the cells and medium from the fermentation is about 0.5 to about 25.

In another aspect, a process for fermentation of syngas includes inoculating a medium to provide an inoculated medium having cell density of at least about 0.1 grams per liter. Inoculated medium is contacted with syngas and upon reaching an ethanol concentration of more than about 10 g/L in the fermentation, cells and medium are removed and separated to provide concentrated cells and permeate. A permeate holding tank receives permeate. A distillation column receives permeate from the permeate holding tank. The distillation column is effective for separating ethanol from the permeate to provide ethanol and a reduced ethanol aqueous stream. The reduced ethanol aqueous stream is returned to the fermentation. In an important aspect, a ratio of a rate of providing the reduced ethanol aqueous stream to the fermentation to a rate of removing the cells and medium from the fermentation is about 0.5 to about 25.

In another aspect, a process for fermentation of syngas includes inoculating a medium to provide an inoculated medium having cell density of at least about 0.1 grams per liter. Cells and medium are removed and separated to provide concentrated cells and permeate. Ethanol is separated from the permeate to provide ethanol and a reduced ethanol aqueous stream. The reduced ethanol aqueous stream is returned to the fermentation. In an important aspect, a rate of providing the reduced ethanol aqueous stream and a rate of removing the cells and medium is effective for providing a growth factor of 0.01 grams/gram/hour (increase in amount of dry weight of cell in grams/gram of dry weight of parent cell/hour).

In another aspect, a process for fermentation of syngas includes inoculating a medium to provide an inoculated medium having cell density of at least about 0.1 grams per liter. Inoculated medium is contacted with syngas. A growth factor is measured and an aqueous stream is returned to the fermentation when the growth factor is less than a critical growth factor.

In another aspect, a process for high productivity fermentation of syngas includes inoculating a medium to provide an inoculated medium having cell density of at least about 0.1 grams per liter. Cells and medium are removed and separated to provide concentrated cells and permeate. Ethanol is separated from the permeate to provide ethanol and a reduced ethanol aqueous stream. The reduced ethanol aqueous stream is returned to the fermentation. In an important aspect, a ratio of a rate of providing the reduced ethanol aqueous stream to the fermentation to a rate of removing the cells and medium from the fermentation is about 0.5 to about 25. The process is effective for maintaining an STY of at least about 60 g/(L·day).

BRIEF DESCRIPTION OF FIGURES

The above and other aspects, features and advantages of several aspects of the process will be more apparent from the following drawings.

Figure 1:
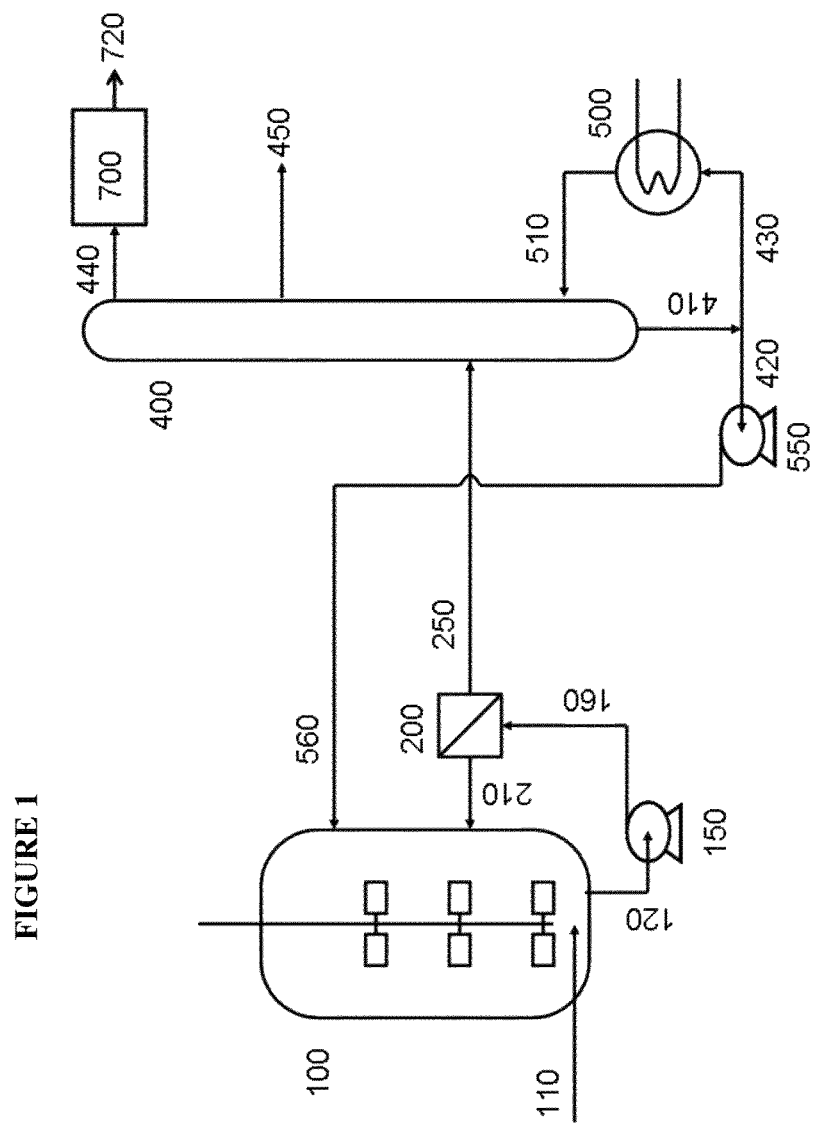
FIG. 1 illustrates a process and system for fermentation of syngas.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Upon startup and subsequent fermentation there is a need to balance cell and medium removal from the fermentor with time required to remove cells from permeate, remove ethanol from permeate, and time required to return a reduced ethanol permeate back to the fermentor. The present process balances these processes to provide a stable startup and subsequent fermentation.

Syngas fermentations conducted in bioreactors with medium and acetogenic bacteria as described herein are effective for providing conversions of CO in syngas into alcohols and other products. In this aspect, productivity may be expressed as STY (space time yield expressed as g ethanol/(L·day). In this aspect, the process is effective for providing a STY (space time yield) of at least about 10 g/(L·day), in another aspect, at least about 30 g/(L·day), in another aspect, at least about 60 g/(L·day), and in another aspect, at least about 90 g/(L·day). Possible STY values include about 10 g/(L·day) to about 200 g/(L·day), in another aspect, about 10 g/(L·day) to about 160 g/(L·day), in another aspect, about 10 g/(L·day) to about 120 g/(L·day), in another aspect, about 10 g/(L·day) to about 80 g/(L·day), in another aspect, about 20 g/(L·day) to about 140 g/(L·day), in another aspect, about 20 g/(L·day) to about 100 g/(L·day), in another aspect, about 40 g/(L·day) to about 140 g/(L·day), and in another aspect, about 40 g/(L·day) to about 100 g/(L·day).

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The term "fermentor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "cell recycle" refers to separation of microbial cells from a fermentation broth and returning all or part of those separated microbial cells back to the fermentor. Generally, a filtration device is used to accomplish separations.

The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

Syngas Fermentation System

FIG. 1 illustrates a process and system for fermentation of syngas. Syngas enters reactor vessel 100 through a syngas inlet 110. Medium and cells and are drawn out through medium outlet 120 and supplied to a cell separation filter 200 through filter supply 160 using a medium recirculation pump 150. The cell separation filter 200 provides concentrated cells and permeate. The reactor vessel 100 receives concentrated cells through cell recycle line 210 and a distillation column 400 receives permeate through a permeate supply 250. The distillation column 400 provides an ethanol/water azeotrope 440 and a reduced ethanol aqueous stream 410. A molecular sieve/dryer 700 may receive the ethanol/water azeotrope 440 and provide ethanol product 720. A reboiler 500 receives a portion of the reduced ethanol aqueous stream 410 through a reboiler supply line 430. The reboiler 500 provides a preheated reduced ethanol aqueous stream 510. An aqueous stream recirculation pump 550 receives the reduced ethanol aqueous stream through aqueous supply line 420. The aqueous stream recirculation pump 550 provides the reduced ethanol aqueous stream back to the reactor vessel 100 through a reduced ethanol aqueous stream supply line 560.

In another aspect, a fusel oil may be removed from the distillation column 400 at side draw 450. As used herein, "fusel oil" may include amyl alcohol, propanol, butanol, fatty acids, esters, and mixtures thereof.

Figure 2:
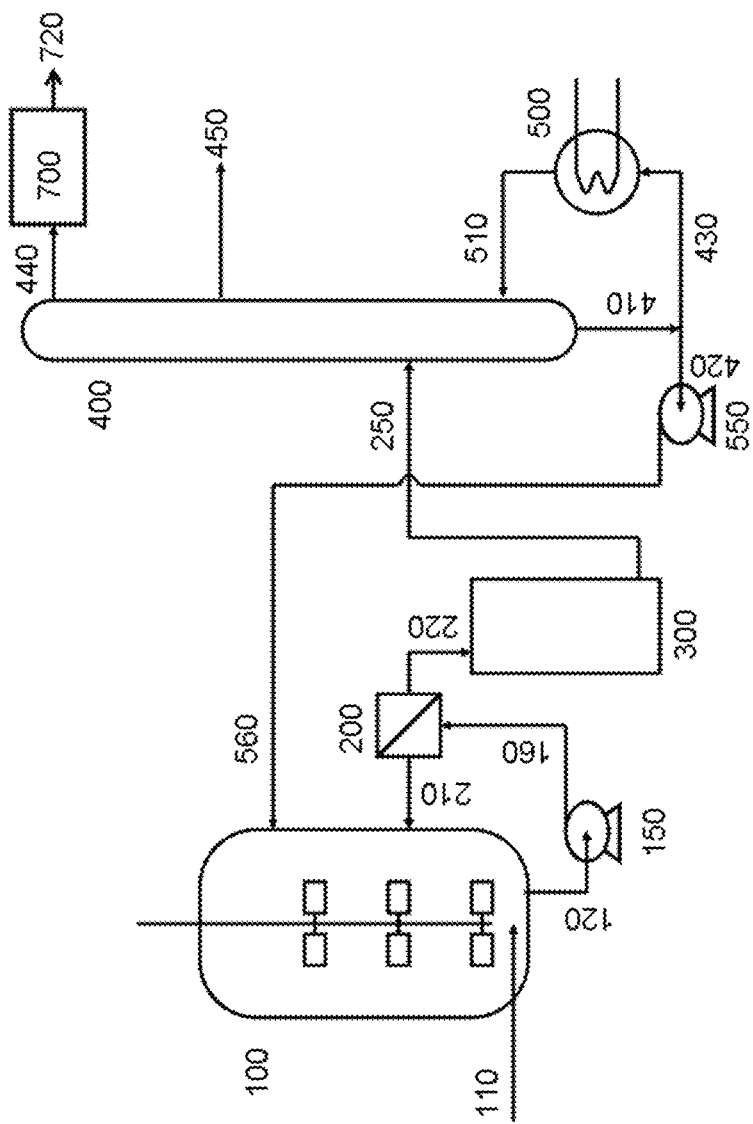
FIG. 2 shows a process and system for fermentation of syngas that includes a permeate holding tank.

FIG. 2 illustrates another aspect of a process and system for fermentation of syngas. The process and system described in FIG. 2 are similar to FIG. 1 and the system and process in FIG. 2 includes a permeate holding tank 300. In this aspect, the permeate holding tank 300 receives permeate from filter 200 through permeate supply line 220. A distillation column 400 receives permeate through a permeate supply line 250. Any of the aspects described herein may include a permeate holding tank.

Figure 3:
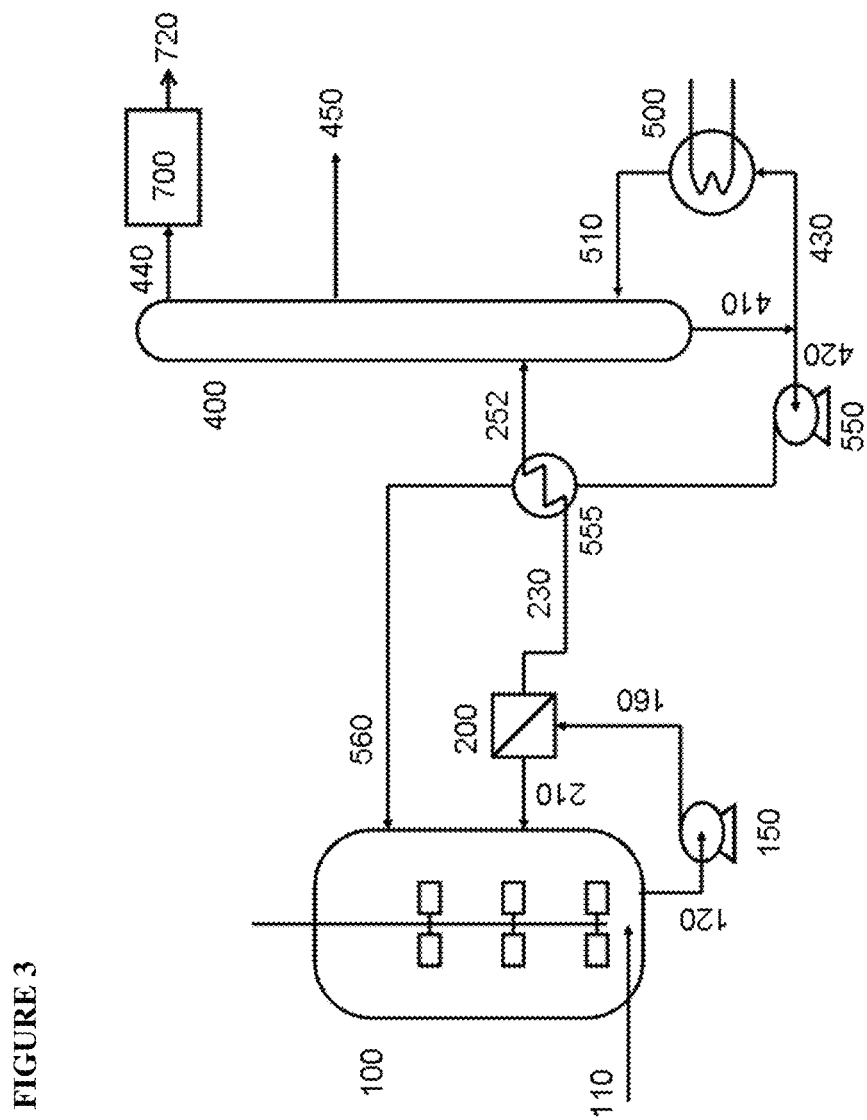
FIG. 3 illustrates a process and system for fermentation of syngas that includes a heat exchanger.

FIG. 3 illustrates another aspect of a process and system for fermentation of syngas. The process and system described in FIG. 3 are similar to FIG. 1 and the system and process in FIG. 3 includes heat exchanger 555. In this aspect, the heat exchanger receives a reduced ethanol aqueous stream and permeate from filter 200 through supply line 230. The heat exchanger 555 is effective for providing a preheated permeate. The distillation column 400 receives the preheated permeate through preheated permeate supply line 252. In this aspect, heat remaining in the reduced ethanol aqueous stream may be utilized to preheat permeate prior to distillation. Any of the aspects described herein may include a heat exchanger.

Figure 4:
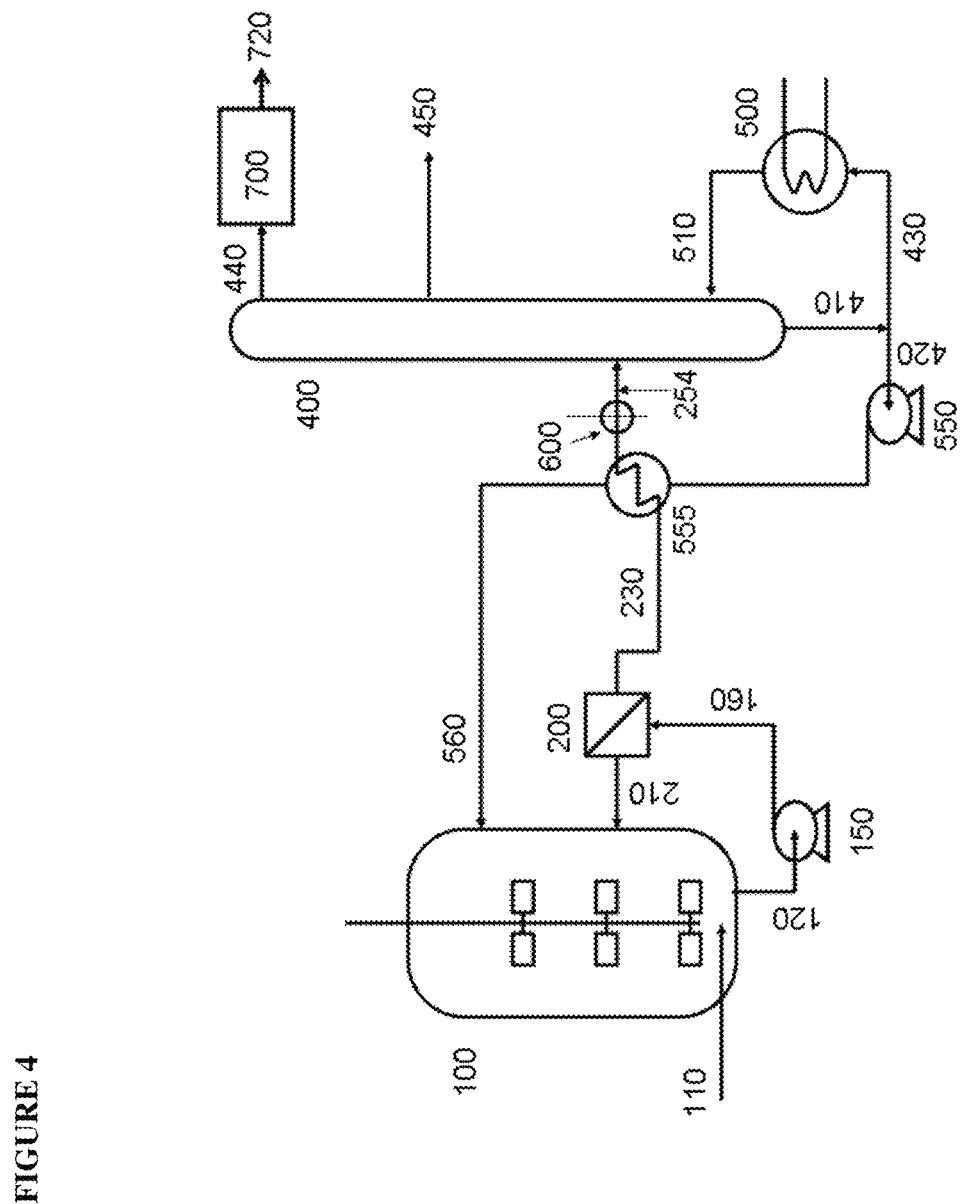
FIG. 4 shows a process and system for fermentation of syngas that includes a heat exchanger and $CO_2$ stripper.

FIG. 4 illustrates another aspect of a process and system for fermentation of syngas. The process and system described in FIG. 4 are similar to FIG. 1 and the system and process in FIG. 4 include a $CO_2$ stripper 600. In this aspect, the $CO_2$ stripper 600 receives permeate and is effective for providing a reduced $CO_2$ permeate. Reduced $CO_2$ permeate will have a lower level of $CO_2$ than prior to stripping. In this aspect, the reduced $CO_2$ permeate will have a reduction in $CO_2$ of about 10% or more, in another aspect, about 25% or more, in another aspect, about 50% or more, in another aspect, about 75% or more, and in another aspect, about 90% or more, as compared to the permeate before $CO_2$ removal. The distillation column 400 receives reduced $CO_2$ permeate through $CO_2$ permeate supply line 254. This aspect may include a heat exchanger 555 as shown and may also include a permeate holding tank.

Figure 5:
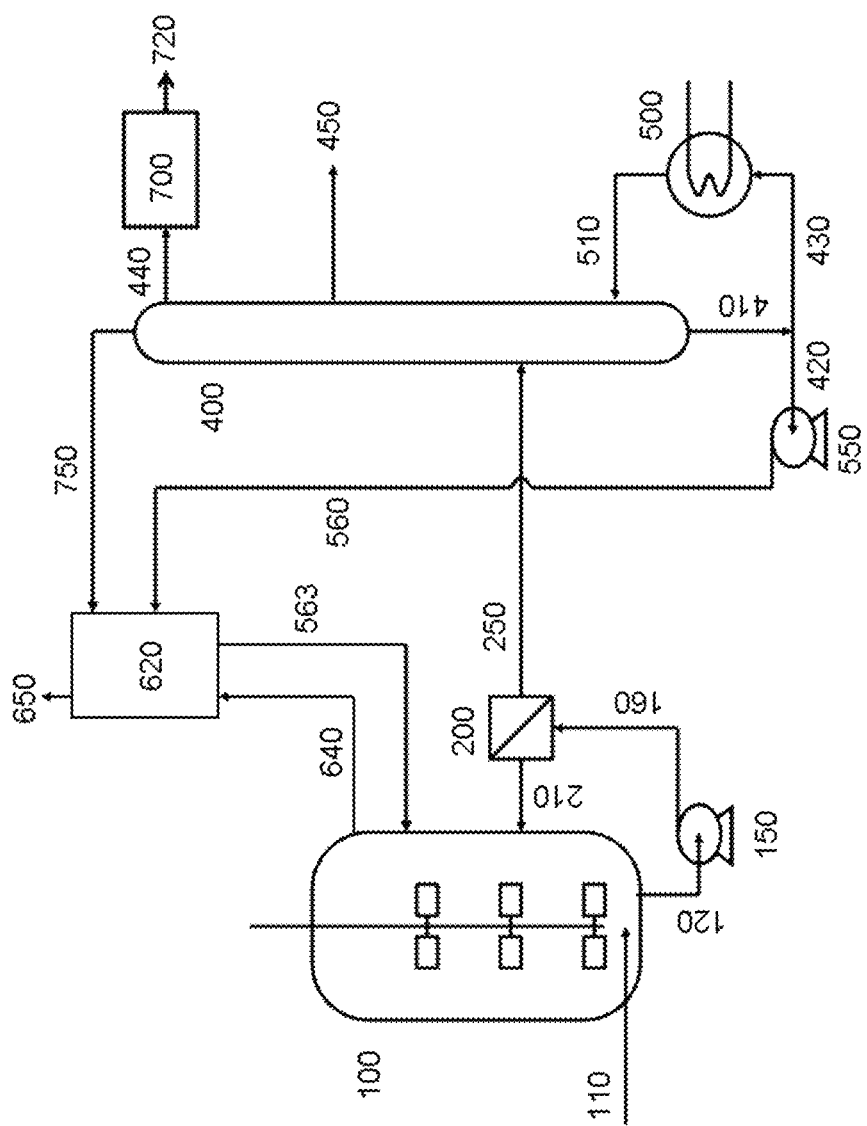
FIG. 5 illustrates a process and system for fermentation of syngas that includes a vent gas scrubber.

FIG. 5 illustrates another aspect of a process and system for fermentation of syngas. The process and system described in FIG. 5 are similar to FIG. 1 and the system and process in FIG. 5 include a vent gas scrubber 620. In this aspect, the vent gas scrubber 620 receives the reduced ethanol aqueous stream through a reduced ethanol supply line 560, vent gas through vent gas supply line 640, and distillation column exhaust gas 750. The vent gas scrubber 620 provides a reduced ethanol aqueous stream back the reactor vessel 100 through aqueous supply line 563 and allows vent gas to vent through vent gas exit 650. The vent gas scrubber may be included in any of the aspects described herein. In one aspect, the vent gas scrubber may be effective for removing ethanol from the fermentor off-gas.

Syngas Fermentation Process

Medium: In accordance with one aspect, the fermentation process is started by addition of a suitable medium to the reactor vessel. The liquid contained in the reactor vessel may include any type of suitable nutrient medium or fermentation broth. The nutrient medium will include vitamins and minerals effective for permitting growth of the microorganism being used. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

Inoculum: In accordance with the process, a culture of acetogenic bacteria are inoculated into a reactor to provide an inoculated medium having a minimum cell density. As used herein, "minimum cell density" means a viable cell density of at least about 0.1 grams per liter, in another aspect, at least about 0.2 grams per liter, in another aspect, at least about 0.3 grams per liter, in another aspect, at least about 0.4 grams per liter, and in another aspect, at least about 0.5 grams per liter. The minimum cell density will not exceed about 1.2 grams per liter. In another aspect, the first culture used to inoculate a pre-reactor or seed reactor has a pH of 6.5 or less, in another aspect 4.5 or less, and in another aspect, about 4.0 to about 4.5. The first culture used to inoculate a reactor has an acetic acid concentration of about 10 grams per liter or less, in another aspect, about 1 to about 10 grams per liter, in another aspect, about 1 to about 5 grams per liter, in another aspect, about 1 to about 3 grams per liter, and in another aspect, about 2 grams per liter.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui*, *Acetoanaerobium noterae*, *Acetobacterium woodii*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum*, *Clostridium pasteurianum* (DSM 525 of DSMZ Germany), *Clostridium ragsdali* P11 (ATCC BAA-622), *Clostridium scatologenes*, *Clostridium thermoaceticum*, *Clostridium ultunense*, *Desulfotomaculum kuznetsovii*, *Eubacterium limosum*, *Geobacter sulfurreducens*, *Methanosarcina acetivorans*, *Methanosarcina barkeri*, *Morrella thermoacetica*, *Morrella thermoautotrophica*, *Oxobacter pfennigii*, *Peptostreptococcus productus*, *Ruminococcus productus*, *Thermoanaerobacter kivui*, and mixtures thereof.

Syngas: Gasification involves partial combustion of biomass in a restricted supply of oxygen. The resultant gas mainly includes CO and $H_2$. In this aspect, syngas will contain at least about 20 mole % CO, in one aspect, about 20 to about 100 mole % CO, in another aspect, about 30 to about 90 mole % CO, in another aspect, about 40 to about 80 mole % CO, and in another aspect, about 50 to about 70 mole % CO. The syngas will have a $CO/CO_2$ ratio of at least about 0.75. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

Syngas is introduced into the bioreactor at a rate effective for maintaining a pressure in the bioreactor of at least about 0 psig, in another aspect, about 0.25 psig, in another aspect, about 0.5 psig, in another aspect about 1 psig, and in another aspect, a pressure of about 10 to about 250 psig. In various other aspect, the pressure may be about 10 to about 200 psig, about 10 to about 100 psig, about 10 to about 75 psig, about 10 to about 50 psig, about 10 to about 25 psig, about 20 to about 250 psig, about 20 to about 200 psig, about 20 to about 100 psig, about 20 to about 75 psig, about 20 to about 50 psig, about 20 to about 25 psig, about 30 to about 250 psig, about 30 to about 200 psig, about 30 to about 100 psig, about 30 to about 75 psig, about 30 to about 50 psig, about 40 to about 250 psig, about 40 to about 200 psig, about 40 to about 100 psig, about 40 to about 75 psig, about 40 to about 50 psig, about 50 to about 250 psig, about 50 to about 200 psig, about 50 to about 100 psig, and about 50 to about 75 psig.

In one aspect, in certain size fermentors, syngas is introduced into the gas inlet/sparger 110 at a rate of about 10 to about 50 ft³/sec, and in another aspect, a rate of about 25 to about 35 ft³/sec. Pressure is controlled through controlling the rate at which syngas is introduced in combination with controlling the rate at which gas is exhausted from the reaction vessel. Pressure may be measured in the reactor headspace or at the bottom of the reactor vessel.

Agitation: Startup agitation is set to about 10 to about 30 Hz, in another aspect about 25 Hz, during inoculation. Agitation ramps up to about 35 to about 50 Hz, in another aspect, about 45 Hz, at a ramping rate of about 2 to about 10 Hz every 10 minutes, and in another aspect, about 5 Hz every 10 minutes.

Cell Recycle: Upon reaching an ethanol concentration of more than about 10 g/liter in the fermentation, the process includes removing cells and medium from the fermentor 100. In another aspect, the process includes removing cells and medium when the fermentation reaches and ethanol concentration of more than about 20 g/liter, and in another aspect, more than about 30 g/liter. Concentrated cells and medium are provided by separating cells from the medium. Separation of cells from medium may be done using known methods, such as for example a cell separation filter 200. As used herein, "concentrated cells" refers to a stream of cells which has a higher density of cells than prior to separation of medium from the cells. "Permeate" refers to the medium after separation of the cells. In this aspect, the permeate may contain ethanol. All or part of the concentrated cells may be returned to the fermentor 100. In one aspect, cell recycle may be started prior to or immediately upon inoculation.

In another aspect, cells and medium may be removed upon reaching a cell density of about 0.5 grams per liter or more, in another aspect, about 0.6 grams per liter or more, in another aspect, about 0.7 grams per liter or more, in another aspect, about 0.8 grams per liter or more, in another aspect about 0.9 grams per liter or more, in another aspect about 1.0 grams per liter or more, in another aspect about 1.5 grams per liter or more, in another aspect about 2.0 grams per liter or more, in another aspect about 2.5 grams per liter or more, in another aspect about 0.5 to about 5.0 grams per liter or more, in another aspect about 1.0 to about 4.0 grams per liter or more, and in another aspect about 2.0 to about 3.0 grams per liter or more.

The process provides for separation of ethanol from permeate to supply ethanol and a reduced ethanol aqueous stream. In one aspect, permeate may be transferred to a permeate holding tank 300 and subsequently transferred to a distillation column 400. In one aspect, upon reaching a volume of at least about 1% to about 100% of a total volume of the permeate holding tank, permeate from the holding tank is continuously transferred to a distillation column 400. In another aspect, transfer of permeate to the distillation column may occur once the permeate holding tank 300 reaches a volume of about 10% of its total volume, in another aspect, at least about 25% of its volume, in another aspect, at least about 50% of its volume, in another aspect, at least about 75% of its volume, and in another aspect, at least about 90% of its volume. The distillation column 400 provides ethanol 450 and a reduced ethanol aqueous stream 410. The distillation column can be any distillation column known in art, e.g. a tray column, a packed column. The distillation column generally produces an ethanol-water azeotrope that is further processed using, for example, a molecular sieve to produce anhydrous ethanol.

As used herein, "reduced ethanol aqueous stream" refers to the aqueous stream after removal of at least a portion of ethanol. The reduced ethanol aqueous stream may include only the reduced ethanol aqueous stream from the distillation column or may include the reduced ethanol aqueous stream from the distillation column in addition to other added medium and/or water. The reduced ethanol aqueous stream is continuously returned to the reactor vessel 100. In this aspect, a ratio of a rate of providing the reduced ethanol aqueous stream to a rate of removing the cells and medium is about 0.5 to about 25, in another aspect, about 0.5 to about 10, in another aspect, about 0.5 to about 5, in another aspect, about 0.5 to about 1, in another aspect, about 1 to about 20, in another aspect, about 5 to about 15, in another aspect, about 5 to about 10, in another aspect, about 4 to about 8, in another aspect, about 5 to about 7, in another aspect, about 5, in another aspect, about 6, and in another aspect, about 7. In this aspect, the reduced ethanol aqueous stream will include less than about 10 weight % alcohol, in another aspect, less than about 5 weight % alcohol, in another aspect, less than about 2.5 weight % alcohol, in another aspect, less than about 1.0 weight % alcohol, in another aspect, less than about 0.5 weight % alcohol, in another aspect, less than about 0.1 weight % alcohol, and in another aspect, less than about 0.01 weight % alcohol.

The reduced ethanol aqueous stream may include acetic acid. In this aspect, the reduced ethanol aqueous stream may have about 5.0 grams per liter acetic acid or less, in another aspect, about 2.5 grams per liter acetic acid or less, in another aspect, about 1.0 grams per liter or less acetic acid, in another aspect, about 0.01 to about 5.0 grams per liter acetic acid, and in another aspect, about 0.01 to about 0.02 grams per liter acetic acid. The reduced ethanol aqueous stream containing acetic acid may be sent back to the reactor such that no net acetic acid is produced. An equilibrium is established between ethanol and water in the reactor. As a result, all CO, $CO_2$ and $H_2$ fed to the reactor may be converted to ethanol, except for that used for culture maintenance.

In another aspect, the rate of providing the reduced ethanol aqueous stream and a rate of removing the cells and medium from the fermentor may be controlled by utilizing a growth factor measurement. As used herein, "growth factor" is the increase in amount of cells (in grams, dry weight) per gram of (parent) cells (dry weight) per hour. In this aspect, the rate of providing the reduced ethanol aqueous stream and a rate of removing the cells and medium is effective for providing a growth factor of at least about 0.01 grams/gram/hour, in another aspect, a growth factor of about 0.01 to about 1, in another aspect, a growth factor of about 0.01 to about 0.5, in another aspect, a growth factor of about 0.01 to about 0.25, and in another aspect, a growth factor of about 0.01 to about 0.1. As used herein "critical growth factor" refers to a minimum desired growth factor. In one aspect, an example of a minimum desired growth factor is about 0.01, in another aspect, about 0.02, and in another aspect, about 0.03. Growth factor may be determined as follows:

$$\text{Growth Factor} = \frac{(\text{Dry wt. of cells in grams at } T_2) - (\text{Dry wt. of cells in grams at } T_1)}{(\text{Dry wt. of cells in grams at } T_1)}$$

where $T_2$ is the dry weight of cells in grams measured at 60 minutes after $T_1$ where $T_1$ is the dry weight of cells in grams at selected starting time.

Figure 6:
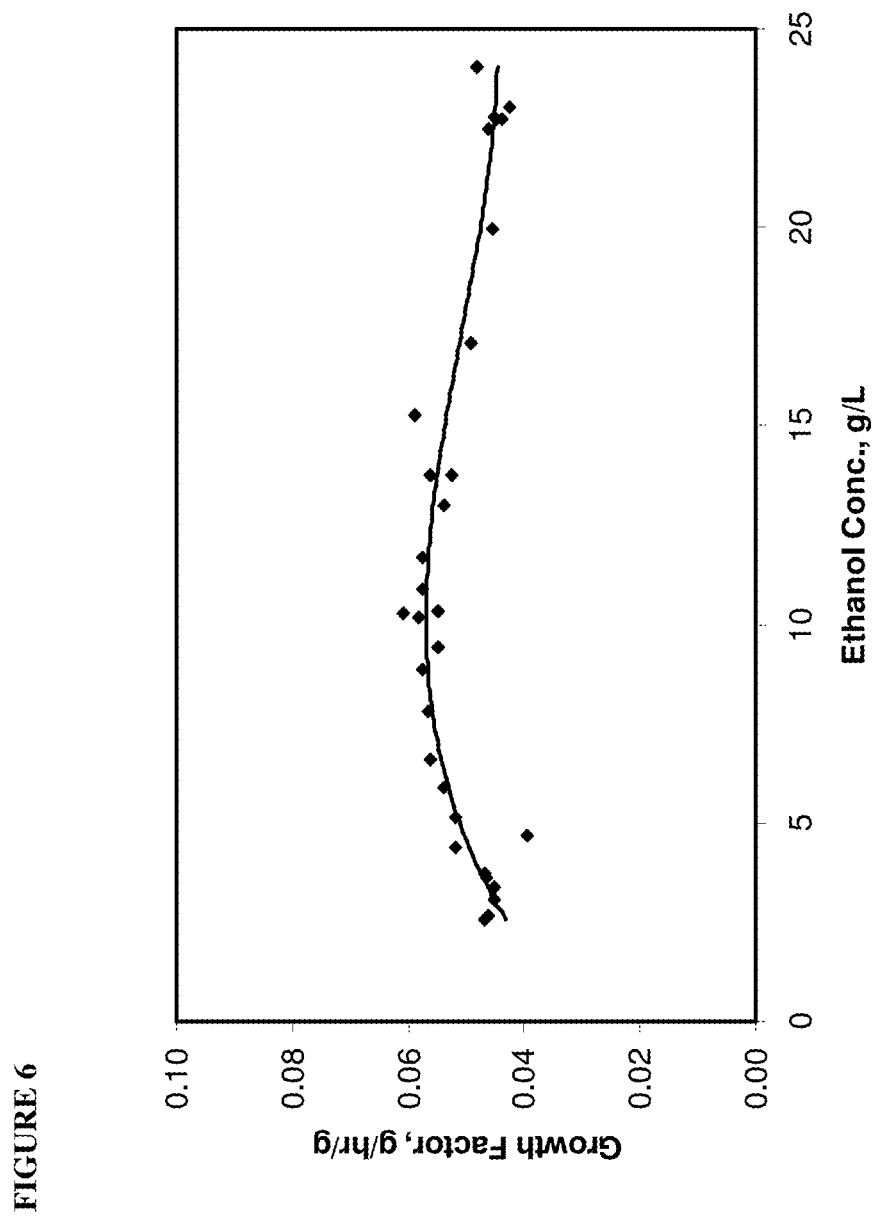
FIG. 6 shows a graph of growth factor vs. ethanol concentration for a culture of acetogenic bacteria.
Figure 7:
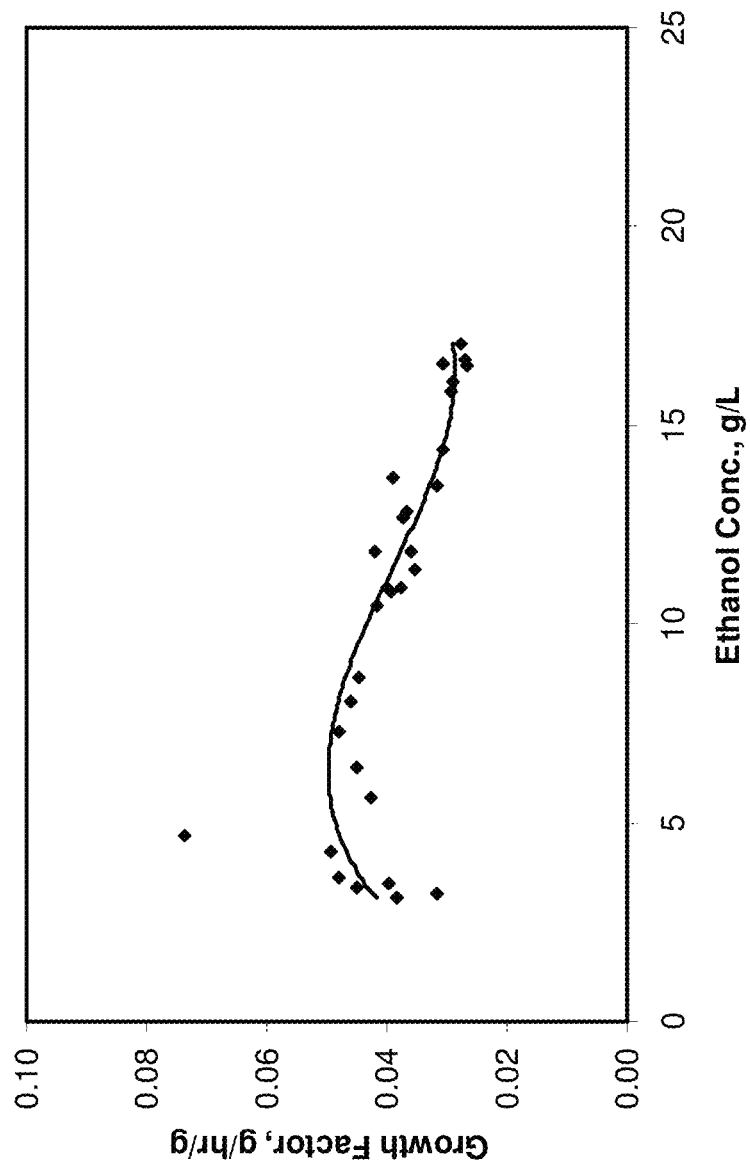
FIG. 7 shows a graph of growth factor vs. ethanol concentration for a culture of acetogenic bacteria.

In this aspect, when the growth factor reaches or goes below a critical growth factor, an aqueous stream is provided to the fermentor. A graph of growth factor vs. ethanol concentration for *Clostridium ljungdahlii* is shown in FIGS. 6 and 7. In this aspect, lower ethanol concentrations may be detrimental or inhibitory for other strains of bacteria.

In one aspect, upon reaching an ethanol concentration of about 10 g/L or more, in another aspect, about 20 g/L or more, and in another aspect, about 30 g/L or more in the fermentation, cells and medium are removed from the fermentation. The cells and medium are separated into ethanol and a reduced ethanol aqueous stream and the reduced ethanol aqueous stream is returned to the fermentation. As further described, any of the described ethanol concentration levels may be utilized in connection with any of the described recycle ratios, cell densities, growth factors and STY values.

In another aspect, upon reaching an ethanol concentration of about 10 g/L or more, the ratio of the rate of providing the reduced ethanol stream to the fermentation to the rate of removing cells and medium from the fermentation is about 0.5 to about 25, in another aspect, about 0.5 to about 10, in another aspect, about 0.5 to about 5, in another aspect, about 0.5 to about 1, in another aspect, about 1 to about 20, in another aspect, about 5 to about 15, in another aspect, about 5 to about 10, in another aspect, about 4 to about 8, and in another aspect, about 5 to about 7, in another aspect, about 5, in another aspect, about 6, and in another aspect, about 7. In a similar aspect, upon reaching an ethanol concentration of about 10 g/L or more and a cell density of about 0.5 g/L or more, in another aspect, about 0.6 g/L or more, in another aspect, about 0.7 g/L or more, in another aspect, about 0.8 g/L or more, in another aspect, about 0.9 g/L or more, in another aspect, about 1.0 g/L or more, in another aspect about 1.5 g/L or more, in another aspect about 2.0 g/L or more, in another aspect about 2.5 g/L or more, in another aspect about 0.5 to about 5.0 g/L, in another aspect about 1.0 to about 4.0 g/L, and in another aspect about 2.0 to about 3.0 g/L, the ratio of the rate of providing the reduced ethanol stream to the fermentation to the rate of removing cells and medium from the fermentation is about 0.5 to about 25, in another aspect, about 0.5 to about 10, in another aspect, about 0.5 to about 5, in another aspect, about 0.5 to about 1, in another aspect, about 1 to about 20, in another aspect, about 5 to about 15, in another aspect, about 5 to about 10, in another aspect, about 4 to about 8, in another aspect, about 5 to about 7, in another aspect, about 5, in another aspect, about 6, and in another aspect, about 7. The process is effective for providing a growth factor of about 0.01 to about 1, in another aspect, about 0.01 to about 0.5, in another aspect, about 0.01 to about 0.25, and in another aspect about 0.01 to about 0.1. The process is further effective for providing an STY of about 10 g/(L·day) to about 200 g/(L·day), in another aspect, about 10 g/(L·day) to about 160 g/(L·day), in another aspect, about 10 g/(L·day) to about 120 g/(L·day), in another aspect, about 10 g/(L·day) to about 80 g/(L·day), in another aspect, about 20 g/(L·day) to about 140 g/(L·day), in another aspect, about 20 g/(L·day) to about 100 g/(L·day), in another aspect, about 40 g/(L·day) to about 140 g/(L·day), and in another aspect, about 40 g/(L·day) to about 100 g/(L·day).

In another aspect, upon reaching an ethanol concentration of about 20 g/L or more, the ratio of the rate of providing the reduced ethanol stream to the fermentation to the rate of removing cells and medium from the fermentation is about 0.5 to about 25, in another aspect, about 0.5 to about 10, in another aspect, about 0.5 to about 5, in another aspect, about 0.5 to about 1, in another aspect, about 1 to about 20, in another aspect, about 5 to about 15, in another aspect, about 5 to about 10, in another aspect, about 4 to about 8, and in another aspect, about 5 to about 7, in another aspect, about 5, in another aspect, about 6, and in another aspect, about 7. In a similar aspect, upon reaching an ethanol concentration of about 10 g/L or more and a cell density of about 0.5 g/L or more, in another aspect, about 0.6 g/L or more, in another aspect, about 0.7 g/L or more, in another aspect, about 0.8 g/L or more, in another aspect, about 0.9 g/L or more, in another aspect, about 1.0 g/L or more, in another aspect about 1.5 g/L or more, in another aspect about 2.0 g/L or more, in another aspect about 2.5 g/L or more, in another aspect about 0.5 to about 5.0 g/L, in another aspect about 1.0 to about 4.0 g/L, and in another aspect about 2.0 to about 3.0 g/L, the ratio of the rate of providing the reduced ethanol stream to the fermentation to the rate of removing cells and medium from the fermentation is about 0.5 to about 25, in another aspect, about 0.5 to about 10, in another aspect, about 0.5 to about 5, in another aspect, about 0.5 to about 1, in another aspect, about 1 to about 20, in another aspect, about 5 to about 15, in another aspect, about 5 to about 10, in another aspect, about 4 to about 8, in another aspect, about 5 to about 7, in another aspect, about 5, in another aspect, about 6, and in another aspect, about 7. The process is effective for providing a growth factor of about 0.01 to about 1, in another aspect, about 0.01 to about 0.5, in another aspect, about 0.01 to about 0.25, and in another aspect about 0.01 to about 0.1. The process is further effective for providing an STY of about 10 g/(L·day) to about 200 g/(L·day), in another aspect, about 10 g/(L·day) to about 160 g/(L·day), in another aspect, about 10 g/(L·day) to about 120 g/(L·day), in another aspect, about 10 g/(L·day) to about 80 g/(L·day), in another aspect, about 20 g/(L·day) to about 140 g/(L·day), in another aspect, about 20 g/(L·day) to about 100 g/(L·day), in another aspect, about 40 g/(L·day) to about 140 g/(L·day), and in another aspect, about 40 g/(L·day) to about 100 g/(L·day).

In another aspect, upon reaching an ethanol concentration of about 30 g/L or more, the ratio of the rate of providing the reduced ethanol stream to the fermentation to the rate of removing cells and medium from the fermentation is about 0.5 to about 25, in another aspect, about 0.5 to about 10, in another aspect, about 0.5 to about 5, in another aspect, about 0.5 to about 1, in another aspect, about 1 to about 20, in another aspect, about 5 to about 15, in another aspect, about 5 to about 10, in another aspect, about 4 to about 8, and in another aspect, about 5 to about 7, in another aspect, about 5, in another aspect, about 6, and in another aspect, about 7. In a similar aspect, upon reaching an ethanol concentration of about 10 g/L or more and a cell density of about 0.5 g/L or more, in another aspect, about 0.6 g/L or more, in another aspect, about 0.7 g/L or more, in another aspect, about 0.8 g/L or more, in another aspect, about 0.9 g/L or more, in another aspect, about 1.0 g/L or more, in another aspect about 1.5 g/L or more, in another aspect about 2.0 g/L or more, in another aspect about 2.5 g/L, in another aspect about 0.5 to about 5.0 g/L, in another aspect about 1.0 to about 4.0 g/L, and in another aspect about 2.0 to about 3.0 g/L, the ratio of the rate of providing the reduced ethanol stream to the fermentation to the rate of removing cells and medium from the fermentation is about 0.5 to about 25, in another aspect, about 0.5 to about 10, in another aspect, about 0.5 to about 5, in another aspect, about 0.5 to about 1, in another aspect, about 1 to about 20, in another aspect, about 5 to about 15, in another aspect, about 5 to about 10, in another aspect, about 4 to about 8, in another aspect, about 5 to about 7, in another aspect, about 5, in another aspect, about 6, and in another aspect, about 7. The process is effective for providing a growth factor of about 0.01 to about 1, in another aspect, about 0.01 to about 0.5, in another aspect, about 0.01 to about 0.25, and in another aspect about 0.01 to about 0.1. The process is further effective for providing an STY of about 10 g/(L·day) to about 200 g/(L·day), in another aspect, about 10 g/(L·day) to about 160 g/(L·day), in another aspect, about 10 g/(L·day) to about 120 g/(L·day), in another aspect, about 10 g/(L·day) to about 80 g/(L·day), in another aspect, about 20 g/(L·day) to about 140 g/(L·day), in another aspect, about 20 g/(L·day) to about 100 g/(L·day), in another aspect, about 40 g/(L·day) to about 140 g/(L·day), and in another aspect, about 40 g/(L·day) to about 100 g/(L·day).

EXAMPLE

Example 1: Effect of Aqueous Recycle on Uptake of $H_2$ and CO

Figure 8:
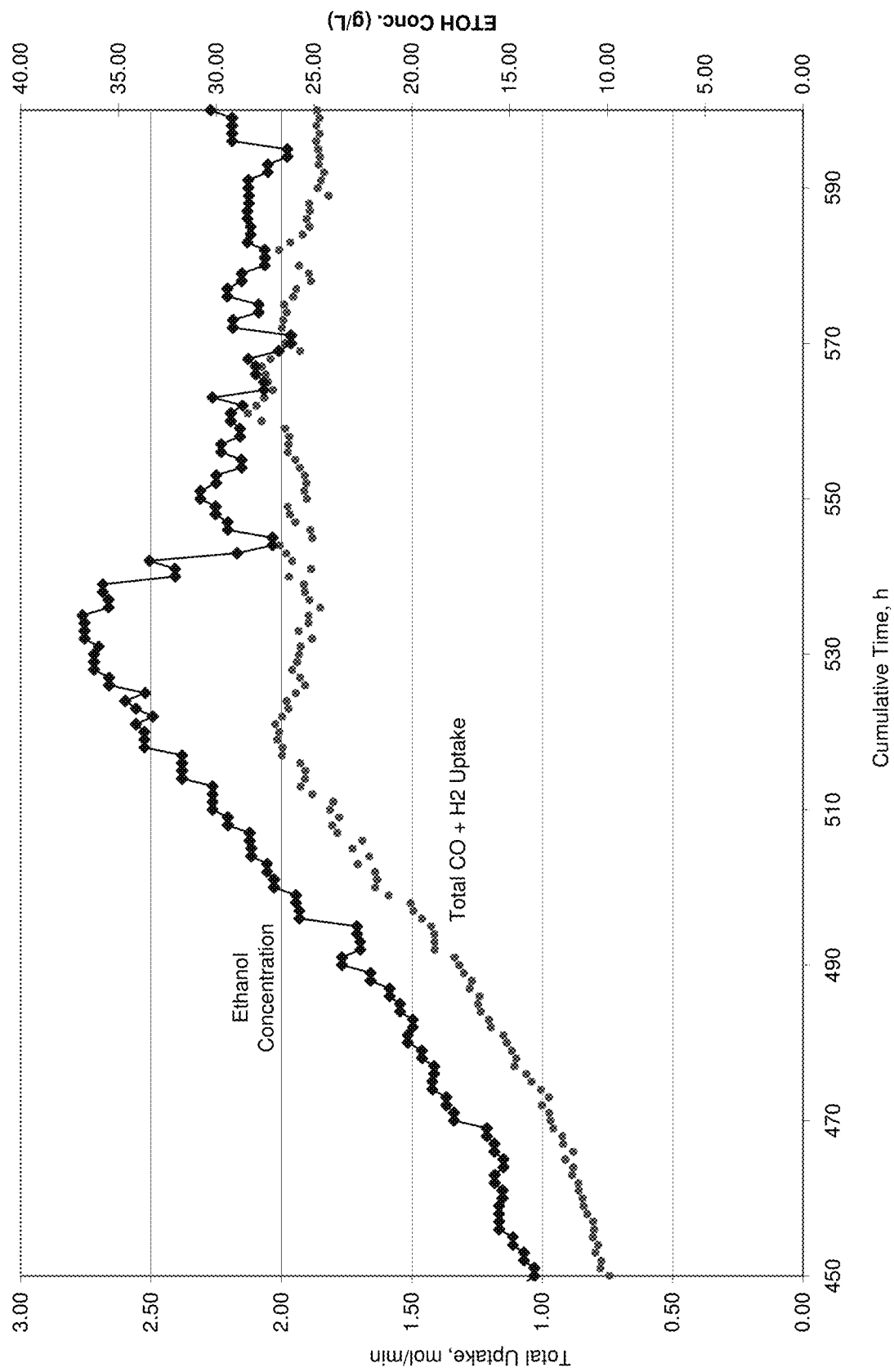
FIG. 8 illustrates the effect of aqueous recycle on ethanol concentration and total uptake of CO and $H_2$.

A fermentation was conducted with *Clostridium ljungdahlii* at a 60 g/L STY level. A graph of ethanol concentration and total $H_2$ and CO uptake are shown in FIG. 8. In this fermentation, water recycle was started once the ethanol concentration exceeded 36.8 g/L. After starting water recycle, ethanol concentration declined to about 28 g/L. Total uptake of $H_2$ and CO reached a maximum at an ethanol concentration of about 33.7 g/L and then decreased from about 2.02 mole/min to about 1.85 mole/min when the ethanol concentration exceeded 36 g/L. Once water recycle was started (about $537^{th}$ hour), ethanol concentration decreased and total $H_2$ and CO uptake increased. Continuing the fermentation without water recycle results in decline in total uptake of total $H_2$ and CO and culture failure.

While the invention herein disclosed has been described by means of specific embodiments, examples and applications thereof, numerous modifications and variations could be made thereto by those skilled in the art without departing from the scope of the invention set forth in the claims.

What is claimed is:

1. A process for reducing ethanol inhibition in fermentation of syngas comprising:
   contacting syngas with a medium inoculated with acetogenic bacteria in a fermentor to provide a minimal cell density of at least about 0.3 grams per liter, providing a startup agitation of about 10 to about 30 Hz, wherein syngas is introduced into the fermentor at a rate to provide a pressure of about 10 to about 50 psig;
   ramping up agitation to about 35 to about 50 Hz at a ramping rate of about 5 Hz every 10 minutes;
   fermenting the syngas to convert CO to ethanol;
   starting to remove cells and medium from the fermentor upon reaching a cell density of about 5 grams per liter or more and an ethanol concentration of more than about 30 g/L in the fermentation;
   separating the removed cells and medium to provide concentrated cells and a permeate, wherein the permeate is transferred to a permeate holding tank located in between the fermentor and a distillation column;
   delivering the permeate to the distillation column and separating the permeate to provide an ethanol, a fusel oil and a reduced ethanol aqueous stream having less than about 5 weight % alcohol;
   recycling a first portion of the reduced ethanol aqueous stream having less than about 5 weight % alcohol to the fermentor;
   sending a second portion of the reduced ethanol aqueous stream having less than about 5 weight % alcohol to a reboiler to produce a preheated reduced ethanol aqueous stream and recycling the preheated reduced ethanol aqueous stream to the distillation column; and
   calculating a growth factor and controlling the rate of recycling the first portion of the reduced ethanol aqueous stream and the rate of removing cells and medium from the fermentor to maintain the growth factor within 0.01 to about 0.25, where the growth factor is an increase in an amount of cells (in gram, dry weight) per gram of (parent) cells (dry weight) per hour;
   wherein an added aqueous stream is provided to the fermentor when the growth factor is less than a critical growth factor of 0.02;
   wherein an aqueous recycle rate is maintained to provide a total $H_2$ and CO uptake of 0.7 to 2.0 mole/min;
   wherein an ethanol concentration of more than about 10 g/L is maintained in the fermentation.

2. The process of claim 1 wherein the reduced ethanol aqueous stream comprises acetic acid.

3. The process of claim 1 wherein $CO_2$ is removed from the permeate prior to distillation.

* * * * *